United States Patent

Sogaro

(10) Patent No.: US 9,579,647 B2
(45) Date of Patent: Feb. 28, 2017

(54) PIPETTE

(75) Inventor: Alberto C. Sogaro, Kronberg (IT)

(73) Assignee: SULZER MIXPAC AG, Haag (DE)

( * ) Notice: Subject to any disclaimer, the term of this patent is extended or adjusted under 35 U.S.C. 154(b) by 669 days.

(21) Appl. No.: 13/129,552

(22) PCT Filed: Sep. 7, 2009

(86) PCT No.: PCT/DE2009/001257
§ 371 (c)(1),
(2), (4) Date: Jun. 17, 2011

(87) PCT Pub. No.: WO2010/054609
PCT Pub. Date: May 20, 2010

(65) Prior Publication Data
US 2011/0243812 A1 Oct. 6, 2011

(30) Foreign Application Priority Data

Nov. 17, 2008 (DE) .................. 20 2008 015 189

(51) Int. Cl.
*B01L 3/02* (2006.01)
*A61C 5/06* (2006.01)

(52) U.S. Cl.
CPC ............ *B01L 3/0293* (2013.01); *A61C 5/062* (2013.01); *B01L 3/021* (2013.01); *B01L 2200/16* (2013.01)

(58) Field of Classification Search
USPC .... 422/500, 501, 100, 520; 73/1.74, 864.01, 73/864.23; 222/209
See application file for complete search history.

(56) References Cited

U.S. PATENT DOCUMENTS

| 5,791,801 | A | * | 8/1998 | Miller ........................... 401/132 |
| 6,059,570 | A | | 5/2000 | Dragon |
| 6,450,810 | B1 | * | 9/2002 | Fischer et al. .................. 433/80 |
| 2002/0160333 | A1 | * | 10/2002 | Pierson et al. .................. 433/90 |
| 2011/0150559 | A1 | * | 6/2011 | Sogaro .......................... 401/268 |

FOREIGN PATENT DOCUMENTS

| EP | 1 743 618 A | 1/2007 |
| EP | 1 797 957 A | 6/2007 |
| EP | 1797957 A1 * | 6/2007 |
| WO | 00/24514 A | 5/2000 |
| WO | 02/36033 A | 5/2002 |
| WO | WO 2005085081 A1 * | 9/2005 |
| WO | 2008/013423 A | 11/2008 |

OTHER PUBLICATIONS

International Search Report corresponding to PCT/DE2009/001257 under date of mailing of Dec. 15, 2009.
PCT, English Translation of International Preliminary Report on Patentability, Application No. PCT/DE2009/001257, May 26, 2011.

* cited by examiner

*Primary Examiner* — Jill Warden
*Assistant Examiner* — Julie Tavares
(74) *Attorney, Agent, or Firm* — Quarles & Brady LLP

(57) ABSTRACT

An apparatus for applying a free-flowing substance including a single piece pipetting tube is manufactured from plastic. The pipetting tube has an exit orifice-leading to the environment at one end and is closed at the other end. An application device proximal the exit orifice can be wetted with the free-flowing substance.

6 Claims, 2 Drawing Sheets

PIPETTE

CROSS-REFERENCE TO RELATED APPLICATIONS

Figure 1:
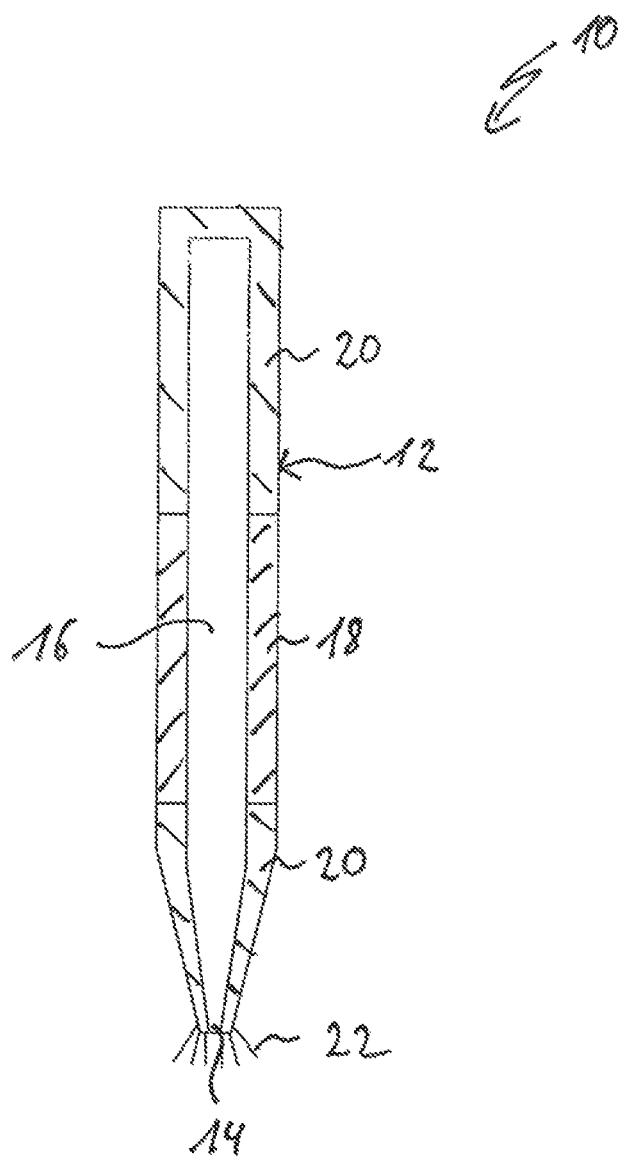

This application claims priority to PCT International Application No. PCT/DE2009/001257filed on Sept. 07, 2009, which claims priority to German Application No. 20 2008 015 189.9filed on Nov. 17, 2008, both of which are fully incorporated by referenced herein.

The invention relates to an apparatus for applying a fluid substance comprising a pipetting tube manufactured from plastics, one end of which has a delivery orifice leading to the environment.

Such pipettes are known in practice, they finding application especially in the laboratory for pipetting or spotting fluid substances. As a rule the delivery orifice is arranged at the bottom end of a substantially tapered portion of the pipetting tube configured as one-piece plastics item. However, using such spotting pipetting tubes makes it difficult to paint a site with the fluid substance to be applied.

This is why the invention is based on the object of providing an apparatus of the generic type as aforementioned which now permits painting the fluid substance to be applied.

This object is achieved in accordance with the invention by the apparatus having the features of claim 1.

Consequently, the subject matter of the invention involves an apparatus for applying a fluid substance comprising a pipetting tube manufactured from plastics in one piece, one end of which has a delivery orifice leading to the environment and its other end is closed off. In the region of the delivery orifice an application device which can be wetted with the fluid substance is provided.

By the application device arranged in the delivery orifice which can be wetted with the fluid substance held in the pipetting tube the fluid substance can now be painted on the site. The apparatus in accordance with the invention is thus particularly suitable for painting application of a fluid substance.

In one preferred embodiment of the apparatus in accordance with the invention the application device constitutes a flock of the pipetting tube which is wetted with the fluid substance on delivery from the inner space.

As an alternative or in addition thereto the application device may comprise a paintbrush tuft injection-molded to the face of the pipetting tube encompassing the delivery orifice.

The paintbrush tuft may be configured in many different ways, it particularly being formed by at least one circular chaplet molded to the face of the pipetting tube encompassing the delivery orifice.

To optimize delivery of the apparatus in accordance with the invention the pipetting tube is configured in one preferred embodiment as a two-component injection molded part wherein a first portion of the pipetting tube serving to deliver the fluid substance is made of an elastomer and at least one second portion adjoining the first portion comprising the delivery orifice is made of a hard plastic.

Further advantages and advantageous aspects of the subject matter of the invention read from the description and claims as evident from the drawing.

Figure 2:
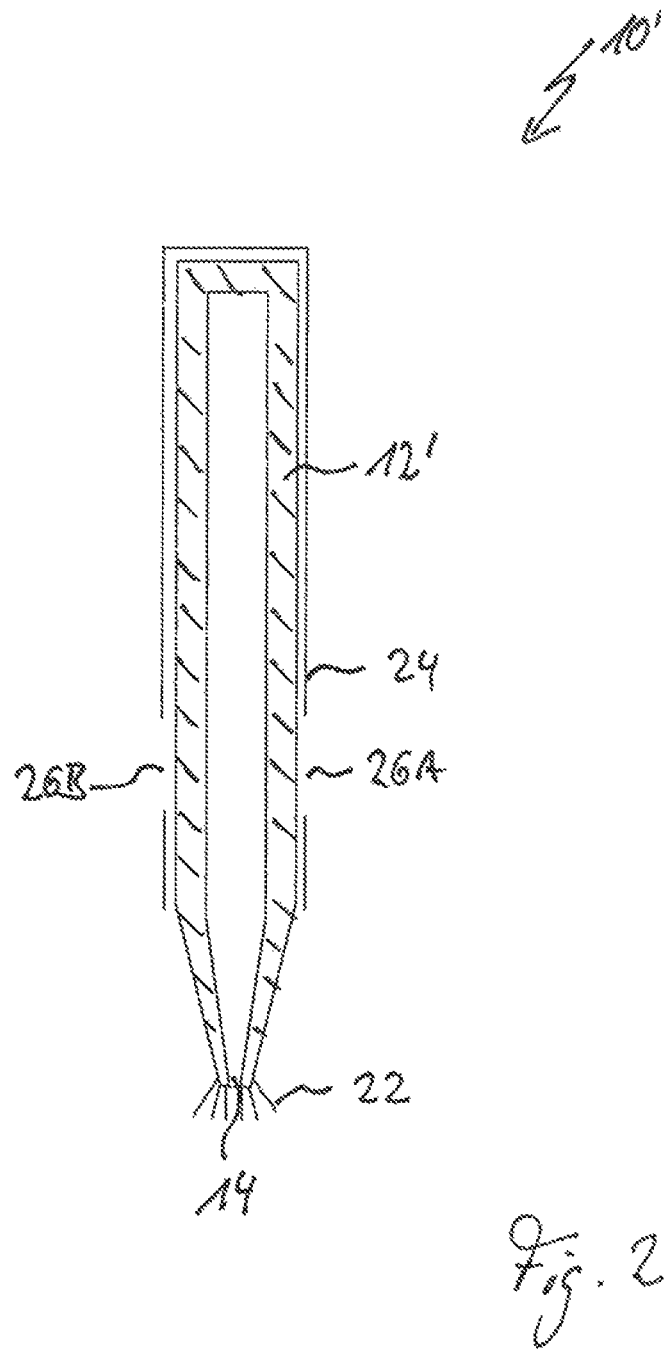

One example embodiment of the apparatus in accordance with the invention is shown diagrammatically simplified in the drawing as detailed in the following wherein FIG. 1 is a longitudinal section through a flocked pipette; and FIG. 2 is a second embodiment of a pipetting apparatus configured in accordance with the invention.

Shown in the drawing is an apparatus 10 configured as a pipette for painting a site for instance a dental tooth stump with a fluid substance. The apparatus 10 comprises a pipetting Pd be 12 ending in a delivery orifice 14 and closed off at the other end opposite the delivery orifice 14. In addition, the pipetting tube 12 comprises an interior space 16 in fluid communication with the delivery orifice 14.

The pipetting tube 12 is a two-component injection molded part comprising a first portion 18 made of a elastically deformable, flexible plastic and two second portions 20 each adjoining the first portion 18 and made of a hard plastic. The second portion 20 bottoming the first portion 18 and incorporating the delivery orifice 14 is tapered in the direction of the delivery orifice 14. A fluid substance held in the interior space 16 can be delivered by the user squeezing the first portion 18 to force the fluid substance through the delivery orifice 14 from the pipetting tube 12.

Furthermore adjoining the delivery orifice 14 rimming the pipetting tube 12 is a flock 22 applied to the second portion 20 of the pipetting tube 12 and which is wetted with the fluid substance from the interior space 16 by the user squeezing the first portion 18. Painting the site with the fluid substance is then done by the flock 22.

Also feasible is to design the pipetting tube 12 in its portion comprising the delivery orifice with a, for example, tubular metal inlay which, on the one hand, stabilizes the pipetting tube 12 and, on the other, may be part of the application device.

In an alternative embodiment of an apparatus 10' in accordance with the invention a pipetting tube 12' made of a flexible, elastic plastic featuring a flock 22 in the region of its delivery orifice is sleeved by an outer tube 24 made of a hard plastic or metal. The outer tube 24 has two scallops 26A and 26B for receiving the linger tips of a user squeezing the inner pipetting tube 12' made of a flexible, elastic plastic so that the fluid substance can be delivered from the pipetting tube 12' for application.

LIST OF REFERENCE NUMERALS 10 pipette
12 pipetting tube
14 delivery orifice
16 inner space
18 first portion
20 second portion
22 flock
24 outer tube
26A,B scallops

The invention claimed is:
1. An apparatus for applying a fluid substance comprising:
a pipetting tube manufactured from plastic as a single piece having a first portion and second portions, said first portion defining an inner space of said pipetting tube and having opposing ends, at least one of said second portions including a delivery orifice in fluid communication with said inner space and leading to the environment, said first portion being an elastically deformable plastic, and each of said second portions being a hard plastic integrally formed with one of the opposing ends of said first portion; and
an application device proximal the delivery orifice which can be wetted with the fluid substance.

2. The apparatus as set forth in claim 1, in which said application device constitutes a flock of the pipetting tube which is wetted with the fluid substance on delivery from the inner space.

3. The apparatus as set forth in claim 1, in which said application device comprises a paintbrush tuft injection-molded to the face of the pipetting tube encompassing the delivery orifice.

4. The apparatus as set forth in claim 3, in which said paintbrush tuft is formed by at least one chaplet.

5. An apparatus for applying a fluid substance comprising:
a molded part having a first portion formed from a first component and two second portions formed from a second component, said first portion defining an inner space of a pipetting tube, one of said second portions being integrally formed with one end of said first portion and including a delivery orifice in fluid communication with said inner space and leading to the environment, the other of said second portions being integrally formed with another end of said first portion, said first component being an elastically deformable plastic, and said second component being a hard plastic, wherein deformation of said first portion urges a fluid substance in said inner space through said delivery orifice of said one of said second portions; and
an application device proximal the delivery orifice which can be wetted with the fluid substance.

6. An apparatus for applying a fluid substance comprising:
a pipetting tube manufactured from elastically deformable plastic as a single piece and defining an inner space in a first portion of said pipetting tube, a second portion integrally formed with said first portion includes a delivery orifice in fluid communication with said inner space and leading to the environment;
an application device proximal the delivery orifice which can be wetted with the fluid substance; and
an outer tube surrounding at least said second portion of said pipetting tube, said outer tube comprising at least two scallops providing access for the user to squeeze the first portion of said pipetting tube through the outer tube.

* * * * *

UNITED STATES PATENT AND TRADEMARK OFFICE
CERTIFICATE OF CORRECTION

PATENT NO. : 9,579,647 B2  
APPLICATION NO. : 13/129552  
DATED : February 28, 2017  
INVENTOR(S) : Alberto C. Sogaro Page 1 of 1

It is certified that error appears in the above-identified patent and that said Letters Patent is hereby corrected as shown below:

In the Specification

Column 2, Line 6: "Pd be" should be --tube--

Column 2, Line 37: "linger" should be --finger--

In the Claims

Column 2, Line 64: "being a hard" should be --being hard--

Signed and Sealed this  
Sixth Day of June, 2017

Michelle K. Lee  
*Director of the United States Patent and Trademark Office*